(12) United States Patent
Kubo et al.

(10) Patent No.: US 8,553,075 B2
(45) Date of Patent: Oct. 8, 2013

(54) ENDOSCOPE APPARATUS AND CONTROL METHOD THEREFOR

(75) Inventors: Masahiro Kubo, Saitama (JP);
Yasunori Ohta, Kanagawa-ken (JP);
Masayuki Takahira, Saitama (JP);
Naoto Kinjo, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 911 days.

(21) Appl. No.: 12/603,187

(22) Filed: Oct. 21, 2009

(65) Prior Publication Data

US 2010/0097454 A1    Apr. 22, 2010

(30) Foreign Application Priority Data

Oct. 22, 2008  (JP) .................................. 2008-271843
Dec. 22, 2008  (JP) .................................. 2005-325256

(51) Int. Cl.
*A62B 1/04*    (2006.01)
*A61B 1/06*    (2006.01)

(52) U.S. Cl.
USPC ................. 348/65; 348/69; 348/70; 600/160; 600/180

(58) Field of Classification Search
USPC ......................... 348/65, 69, 70; 600/160, 180
See application file for complete search history.

(56) References Cited

U.S. PATENT DOCUMENTS

| | | | |
|---|---|---|---|
| 6,582,362 B2 | 6/2003 | Konno | |
| 2004/0130651 A1 | 7/2004 | Wakashiro | |
| 2004/0215060 A1* | 10/2004 | Ueno et al. | 600/160 |
| 2005/0117028 A1 | 6/2005 | Imaizumi et al. | |
| 2006/0029284 A1* | 2/2006 | Stewart | 382/255 |
| 2007/0040906 A1* | 2/2007 | Iketani | 348/69 |
| 2007/0047794 A1 | 3/2007 | Lang et al. | |
| 2007/0055104 A1* | 3/2007 | Kumei et al. | 600/176 |
| 2009/0156901 A1* | 6/2009 | Gono | 600/180 |
| 2009/0208071 A1* | 8/2009 | Nishimura et al. | 382/128 |

FOREIGN PATENT DOCUMENTS

| | | |
|---|---|---|
| EP | 2002-253488 A | 9/2002 |
| EP | 1 527 730 A1 | 5/2005 |
| EP | 1 624 672 A1 | 2/2006 |
| EP | 2007-54115 A | 3/2007 |
| EP | 1 787 577 A1 | 5/2007 |
| JP | 2002-95635 A | 4/2002 |
| JP | 2003-93336 A | 4/2003 |
| JP | 2007-20728 A | 2/2007 |
| WO | WO-2004/039250 A1 | 5/2004 |
| WO | WO-2008/024419 A1 | 2/2008 |

* cited by examiner

*Primary Examiner* — Rupal Dharia
*Assistant Examiner* — Van Kim T Nguyen
(74) *Attorney, Agent, or Firm* — Birch, Stewart, Kolasch & Birch, LLP (57) ABSTRACT

An endoscope image is obtained by imaging a subject with a scope. Then, an edge portion of the endoscope image is extracted and a complexity degree of the edge portion is detected. Thereafter, a determination is made as to whether the endoscope image is an image obtained through near view imaging or distant view imaging according to the complexity degree and an imaging condition is changed according to the determined near view imaging or distant view imaging.

15 Claims, 8 Drawing Sheets

FIG.2

NEAR VIEW ENLARGEMENT MODE

FIG.3

DISTANT VIEW MODE

ENDOSCOPE APPARATUS AND CONTROL METHOD THEREFOR

BACKGROUND OF THE INVENTION

1. Field of the Invention

The present invention relates to an endoscope apparatus capable of controlling various imaging modes and a control method therefor.

2. Description of the Related Art

Endoscope apparatuses for obtaining an image of a body cavity, such as esophagus, stomach, large intestine, and the like, by inserting a scope inside of the body cavity are used in order to perform image diagnosis for the state of the body cavity. Recently, when performing image diagnosis through the endoscope, it has become possible that an endoscope image obtained by the scope is displayed on a monitor in real time and the doctor is able to perform image diagnosis while confirming the imaged area with the monitor.

In order to facilitate image diagnosis, various observation modes using the endoscope are available, including ordinary observation mode in which a subject illuminated with white light is observed, fluorescence observation mode in which fluorescence emitted from a subject when illuminated with excitation light is observed, narrowband mode in which a subject illuminated with narrowband light is observed, and the like.

Here, in order to assist a doctor in performing image diagnosis efficiently, a method for automatically switching these modes is proposed as described, for example, in Japanese Unexamined Patent Publication No. 2007-020728. Japanese Unexamined Patent Publication No. 2007-020728 proposes an automatic switching method among the ordinary observation mode, narrowband observation mode and fluorescence observation mode described above according to the magnification of the lens.

A method for automatically changing the magnification of the imaging lens attached to the tip of the scope according to the imaging mode is also proposed as described, for example, in U.S. Pat. No. 6,582,362. More specifically, U.S. Pat. No. 6,582,362 proposes a method that, based on the fact that, under AEC (auto exposure control) for controlling the aperture of the light source unit to keep the brightness of an image constant, if the distance to the object is changed, the aperture is also changed, determines if it is near view imaging or distant view imaging by figuring out the distance to the object from the state of the aperture and performs high frequency component enhancement processing if the image is an image obtained by near view imaging or low frequency enhancement processing if the image is an image obtained by distant view imaging.

In addition to the method for measuring the distance between the scope and subject using AEC as described in U.S. Pat. No. 6,582,362, there is a demand for a method that enables efficient image diagnosis by automatically switching between near view imaging and distant view imaging according to the imaging region.

Therefore, it is an object of the present invention to provide an endoscope apparatus capable of automatically switching imaging modes according to the type of a subject, and a control method therefor.

As for the narrowband observation mode, for example, Japanese Unexamined Patent Publication No. 2002-095635 proposes an apparatus that emits narrowband light to a living tissue using a narrowband filter to obtain a narrowband image that allows a high contrast observation of a blood vessel or the like on a surface layer of a mucous membrane and displays the narrowband image.

In the mean time, Japanese Unexamined Patent Publication No. 2003-093336 proposes an apparatus that performs a matrix operation on a color image signal obtained with a wide wavelength range without using an optical narrowband filter to obtain a spectrally estimated image which is equivalent to that obtainable using the narrowband filter and displays the spectrally estimated image.

The narrowband image obtained by the apparatus described in Japanese Unexamined Patent Publication No. 2002-095635, however, is an image obtained by emitting light transmitted through the narrowband filter, thus causing a disadvantage that the amount of light emitted to a living tissue is insufficient and the image becomes dark. This disadvantage particularly becomes significant when a distant view image is obtained. In the mean time, the spectrally estimated image obtained by the apparatus described in Japanese Unexamined Patent Publication No. 2003-093336 has sufficient brightness, but the wavelength estimation by the matrix operation has limitations on the accuracy, whereby the image quality may be degraded compared to the narrowband image. This disadvantage becomes more significant when a near view enlarged image is obtained.

In view of the circumstances described above, it is a further object of the present invention to provide an image obtaining method and an endoscope apparatus capable of obtaining an appropriate image in both distant view imaging and near view enlargement imaging.

SUMMARY OF THE INVENTION

An endoscope apparatus of the present invention is an apparatus, including:

a scope for obtaining an endoscope image by imaging a subject;

an edge extraction means for extracting an edge component of the endoscope image obtained by the scope;

a complexity degree detection means for detecting a complexity degree of the edge component extracted by the edge extraction means;

an imaged state determination means for determining whether the endoscope image is an image obtained through near view imaging or distant view imaging of the subject according to the complexity degree detected by the complexity degree detection means; and a condition changing means for changing an imaging condition according to the near view imaging or distant view imaging determined by the imaged state determination means.

An endoscope apparatus control method of the present invention is a method for controlling an endoscope apparatus that obtains an endoscope image by imaging a subject with a scope, the method including the steps of:

extracting an edge component of the endoscope image obtained by the scope;

detecting a complexity degree of the extracted edge component;

determining whether the endoscope image is an image obtained through near view imaging or distant view imaging of the subject according to the detected complexity degree; and changing an imaging condition according to the determined near view imaging or distant view imaging.

Here, the endoscope image may be any image as long as it is obtained by the scope and it may be, for example, an ordinary observation image obtained by emitting white light to the subject, a fluorescence image obtained by emitting excitation light to the subject and imaging fluorescence emitted from the subject, a narrowband image obtained by emitting narrowband image, or a spectral image.

The term "near view imaging" as used herein refers to that the imaging takes place with a tip portion of the scope or a hood attached to the tip portion of the scope is in contact with the subject or slightly away from the subject, and the term "distant view imaging" refers to that the imaging takes place with the tip portion of the scope kept at a distance from the subject.

Further, the imaging condition may be any condition appropriated for the near view imaging or distant view imaging, and refers to any known imaging condition, such as imaging magnification, electronic zoom magnification, amount of light emitted to the subject, or image processing condition.

Still further, the imaged state determination means may be a means that determines the endoscope image to be an image obtained by the near view imaging if the complexity degree is not less than a set threshold value and to be an image obtained by the distant view imaging if the complexity degree is less than the set threshold value.

Further, the complexity degree detection means may employ any method as long as it is capable of detecting the complexity degree of an edge component. For example, it may be a method that detects a fractal dimension of the edge complement as the complexity degree or a method that extracts a pit pattern from the edge component and detects a complexity degree of the detected pit pattern.

Still further, the scope may be a scope having an imaging lens changeable in imaging magnification, and the condition changing means may be a means that increases the magnification of the imaging lens for the near view imaging and decreases the magnification of the imaging lens for the distant view imaging.

Further, the scope may be a scope having a light emitting means for emitting light to the subject, and the condition changing means may be a means that decreases the amount of the light emitted from the light emitting means for the near view imaging and increases the amount of the light emitted from the light emitting means for the distant view imaging.

An image obtaining method of the present invention is a method for use in an endoscope apparatus that includes a scope having an image sensor for picking up an image of an observation target, the method including the steps of:

enabling illumination light and narrowband light to be switchably emitted to the observation target;

enabling switching between an estimated spectral image signal obtaining mode, in which the illumination light is emitted to the observation target and an estimated spectral image signal is obtained by performing spectral image processing, using a predetermined signal processing parameter, on an image signal outputted from the image sensor by the emission of the illumination light, and a narrowband image signal obtaining mode, in which the narrowband light is emitted to the observation target and a narrowband image signal outputted from the image sensor by the emission of the narrowband light is obtained;

obtaining a parameter according to a distance between a tip portion of the scope and the observation target;

performing a threshold judgment on the obtained parameter and accepting a switching signal for switching between the estimated spectral image signal obtaining mode and the narrowband image signal obtaining mode; and obtaining the estimated spectral image signal or the narrowband image signal by switching between the estimated spectral image signal obtaining mode and the narrowband image signal obtaining mode based on a result of the threshold judgment and the switching signal.

An endoscope apparatus of the present invention is an apparatus, including:

a light source unit capable of switchably outputting illumination light and narrowband light to be emitted to an observation target;

a scope having an image sensor for picking up an image of the observation target by receiving reflected light reflected from the observation target by the emission of the illumination light or the narrowband light to the observation target;

a parameter obtaining unit for obtaining a parameter according to a distance between a tip portion of the scope and the observation target;

a threshold judgment unit for performing a threshold judgment on the parameter obtained by the parameter obtaining unit;

a spectral image obtaining unit for obtaining an estimated spectral image signal by performing spectral image processing, using a predetermined signal processing parameter, on an image signal outputted from the image sensor by the emission of the illumination light to the observation target;

a narrowband image obtaining unit for obtaining a narrowband image signal outputted from the image sensor by the emission of the narrowband light to the observation target;

a switching signal accepting unit for accepting a switching signal for switching between obtaining of the estimated spectral image signal and obtaining of the narrowband image signal; and a control unit for switching between emission of the illumination light and emission of the narrowband light in the light source unit based on a judgment result of the threshold judgment unit and the switching signal, and controlling the light source unit, spectral image obtaining unit, and narrowband image obtaining unit to cause switching between obtaining of the estimated spectral image signal and obtaining of the narrowband image signal.

In the endoscope apparatus of the present invention described above, the control unit may be a unit that sets a switchable state when the judgment result of the threshold judgment unit is changed and, if a switching signal is accepted by the switching signal accepting unit after the switchable state has been set, performs switching between emission of the illumination light and emission of the narrowband light and switching between obtaining of the estimated spectral image signal and obtaining of the narrowband image signal.

Further, the control unit may be a unit that, if a switching signal is not received by the switching signal accepting unit for a certain time after the switchable state has been set, terminates the switchable state.

Still further, the control unit may be a unit that, if a switching signal is not received by the switching signal accepting unit for a certain time after the switchable state has been set, performs switching between emission of the illumination light and emission of the narrowband light and switching between obtaining of the estimated spectral image signal and obtaining of the narrowband image signal regardless of whether or not a switching signal is received.

Further, the endoscope apparatus may further include a notification unit for notifying that the apparatus is set to the switchable state.

Still further, the scope may be a scope having an imaging lens for forming an image of the observation target on the image sensor by optically changing the magnification of the image, and the parameter may be a value representing the magnification of the imaging lens.

Further, the apparatus may further include a digital zoom processing unit that performs digital zoom processing on an image signal outputted from the image sensor, and the parameter may be a value representing a magnification of the digital zoom processing.

Still further, the parameter may be luminance information of an image signal outputted from the image sensor.

According to the endoscope apparatus and control method therefor of the present invention, an edge component of the endoscope image obtained by the scope is extracted, then a complexity degree of the extracted edge component is detected, a determination is made as to whether the endoscope image is an image obtained through near view imaging or distant view imaging of the subject according to the detected complexity degree, and an imaging condition is changed according to the determined near view imaging or distant view imaging. This allows a subject the operator intends to observe to be presumed from the endoscope image and an imaging mode appropriate for the observation target region to be set, so that the operator does not need to perform the mode switching and may perform image diagnosis efficiently.

When the imaged state determination means is a means that determines the endoscope image to be an image obtained by the near view imaging if the complexity degree is not less than a set threshold value and to be an image obtained by the distant view imaging if the complexity degree is less than the set threshold value, an accurate determination may be made as to whether or not the endoscope image is an image obtained by the near view imaging based on the fact that densely congregated fine capillary images, surface irregularities, and the like will appear in an endoscope image in the case of near view imaging.

Further, if the complexity degree detection means is a means that detects a fractal dimension of the edge component as the complexity degree, the complexity degree may be detected accurately.

Still further, if the complexity degree detection means is a means that detects the complexity degree of the edge component by extracting a pit pattern from the edge component and detecting a complexity degree of the extracted pit pattern, the complexity degree may be detected accurately.

Further, if the scope is a scope having an imaging lens changeable in imaging magnification, and the condition changing means is a means that increases the magnification of the imaging lens for the near view imaging and decreases the magnification of the imaging lens for the distant view imaging, an appropriate imaging magnification is set automatically for each of the near view imaging and distant view imaging, thereby facilitating efficient image diagnosis.

Still further, if the scope is a scope having a light emitting means for emitting light to the subject, and the condition changing means is a means that decreases the amount of the light emitted from the light emitting means for the near view imaging and increases the amount of the light emitted from the light emitting means for the distant view imaging, an appropriate amount of light is set automatically for each of the near view imaging and distant view imaging, thereby facilitating efficient image diagnosis.

According to the image obtaining method and endoscope apparatus of the present invention, a parameter according to a distance between a tip portion of the scope and the observation target is obtained, then a threshold judgment is performed on the obtained parameter and a switching signal for switching between the estimated spectral image signal obtaining mode and the narrowband image signal obtaining mode is accepted, and the estimated spectral image signal or the narrowband image signal is obtained by switching between the estimated spectral image signal obtaining mode and the narrowband image signal obtaining mode based on a result of the threshold judgment and the switching signal. This allows an estimated spectral image signal to be obtained in distant view imaging in which the edge portion of the scope and observation target are at a distant, and a narrowband image signal to be obtained in near view imaging in which the edge portion of the scope and observation target are close to each other, so that an appropriate image may be displayed according to the distance between the tip portion of the scope and observation target.

Further, according to the image obtaining method and endoscope apparatus of the present invention, the signal obtaining mode is changed based not only on the threshold judgment result of the parameter according to the distance between the tip portion of the scope and observation target but also on the switching signal for switching between the estimated spectral image signal obtaining mode and narrowband image signal obtaining mode. This may prevent display of an image difficult to view due to frequent mode change according to the movement of the tip portion of the scope.

Still further, in the image obtaining method and endoscope apparatus of the present invention, if a switchable state is set when the judgment result of the threshold judgment unit is changed and, if a switching signal is not received by the switching signal accepting unit for a certain time after the switchable state has been set, the switchable state is terminated, control more considering the intention of the operator may be implemented.

Further, if a switching signal is not received by the switching signal accepting unit for a certain time after the switchable state has been set, switching between output of the illumination light and output of the narrowband light and switching between obtaining of the estimated spectral image signal and obtaining of the narrowband image signal are performed regardless of whether or not a switching signal is received, an instruction for the switching by the operator may be skipped.

Still further, if a notification that the apparatus is set to the switchable state is made, the operator may know that the apparatus becomes switchable, so that switching between obtaining of the estimated spectral image signal and obtaining of the narrowband image signal may be made at a better timing.

DESCRIPTION OF THE PREFERRED EMBODIMENTS

Figure 1:
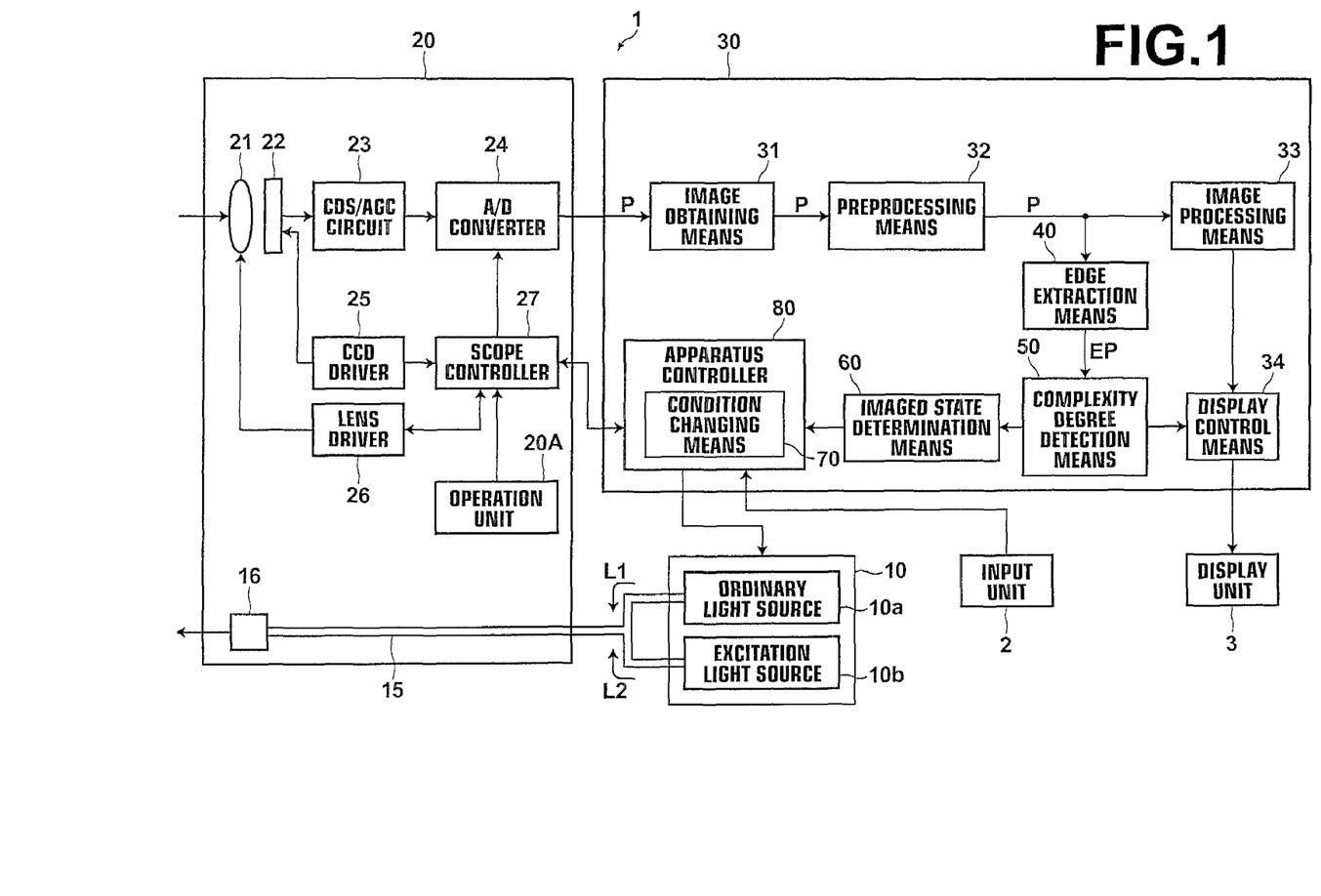
FIG. 1 is a block diagram of a first embodiment of the endoscope apparatus of the present invention.

Hereinafter, a first embodiment of the present invention will be described in detail with reference to the accompanying drawings. FIG. 1 is a block diagram of an example of endoscope apparatus incorporating a first embodiment of the present invention. Endoscope apparatus 1 includes light source unit 10, scope 20, and image processing unit 30. Light source unit 10 is a unit for emitting light to a subject when observing the subject by the endoscope apparatus. Light source unit 10 includes ordinary light source 10*a*, such as a xenon lamp or the like, for an ordinary observation and excitation light source 10*b* for a fluorescence observation, the operation of which is controlled by apparatus controller 80. Ordinary light source 10*a* emits white light and excitation light source 10*b* emits excitation light as described above, the wavelength of which is, for example, 682 nm or 747 nm. Light source unit 10 is optically linked to light guide 15 of scope 20, and white light L1 or excitation light L2 emitted from light source unit 10 is inputted to light guide 15 and emitted to a subject from an observation window (light emitting means) 16. The amount of light emitted from observation window (light emitting means) 16, therefore, is controlled by apparatus controller 80.

Scope 20 includes imaging lens 21, image sensor 22, CDS/AGC circuit 23, A/D converter 24, CCD driver 25, lens driver 26, and the like, each of which is controlled by scope unit controller 27. Imaging lens 21 includes, for example, a plurality of lenses and the imaging magnification is changed by the driving of lens driver 26. Image sensor 22 is, for example, a CCD or a CMOS, and obtains an image by photoelectrically converting a subject image formed by imaging lens 21. As for image sensor 22, for example, a complementary color type having color filters of Mg (magenta), Ye (yellow), Cy (cyan), and G (green) on the image forming plane or a primary color type having RGB color filters on the image forming plane is used. The operation of image sensor 22 is controlled by CCD driver 25. When an image (picture) signal is captured by image sensor 22, the signal is sampled and amplified by CDS/AGC (correlated double sampling/automatic gain control) circuit 23, and the endoscope image outputted from CDS/AGC circuit 23 is A/D converted by A/D converter 24 and outputted to image processing unit 30.

Image processing unit 30 is a unit for processing an endoscope image obtained by scope 20 and includes, for example, a DSP. Image processing unit 30 includes image obtaining means 31, preprocessing means 32, image processing means 33, and display control means 34. Image obtaining means 31 is a means for obtaining an endoscope image P picked up by image sensor 22 of scope 20. Preprocessing means 32 is a means for performing preprocessing on the endoscope image P obtained by image obtaining means 31. Preprocessing means 32 has a function to convert the endoscope image P to a RGB color image if it is an YCC color image, as well as gamma conversion function, gradation adjustment function, and the like. Image processing means 33 is a means for performing enhancement processing and the like on the preprocessed endoscope image P, and display control means 34 has a function to display the endoscope image P processed by image processing means 33 on display unit 3 together with character information.

Image processing unit 30 further includes edge extraction means 40, complexity degree detection means 50, imaged state determination means 60, and condition changing means 70. Edge extraction means 40 is a means for extracting a blood vessel image from the endoscope image preprocessed by preprocessing means 32. Here, edge extraction means 40 detects an edge portion using a known method, such as differential filtering method or the like.

Figure 2:
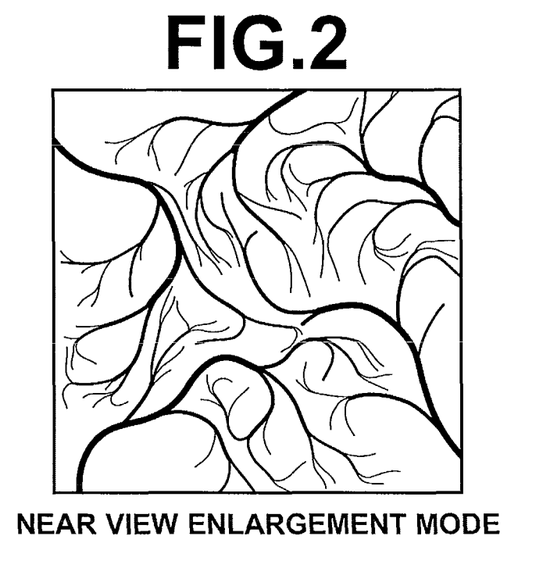
FIG. 2 is a schematic view of an example of endoscope image obtained, in near view imaging, by the endoscope apparatus of FIG. 1.
Figure 3:
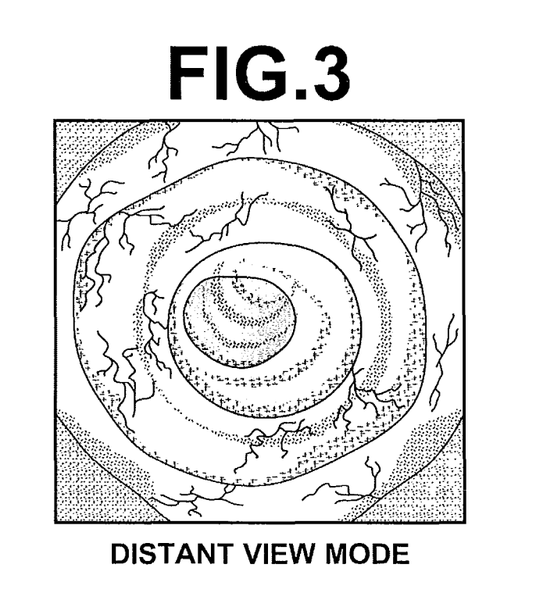
FIG. 3 is a schematic view of an example of endoscope image obtained, in distant view imaging, by the endoscope apparatus of FIG. 1.

Complexity degree detection means 50 is a means for detecting a complexity degree CD of an edge portion EP extracted by edge extraction means 40. More specifically, complexity degree detection means 50 digitizes the edge portion EP and detects a fractal dimension of the digitized edge portion as the complexity degree CD by a known method, such as box counting method. The complexity degree (fractal dimension) CD takes a high value as the structure of the edge portion EP becomes complex and a low value as the structure becomes simple (FIGS. 2 and 3).

Imaged state determination means 60 is a means for determining whether the image is an image obtained by near view imaging or distant view imaging a subject. The term "near view imaging" as used herein refers to that the imaging takes place with a tip portion of scope 20 or a hood attached to the tip of scope 20 is in contact with a subject or slightly away from the subject, and the term "distant view imaging" refers to that the imaging takes place with the tip portion of scope 20 kept at a distance from the subject. Here, imaged state determination means 60 determines an image as near view imaging if the complexity degree CD is not less than a set threshold value CDref and as distant view imaging if the complexity degree CD is less than the set threshold value CDref. In this way, by making use of the fact that, in the near view imaging, densely congregated fine capillary images or irregularities on the surface of a subject will appear in the endoscope image P and the complexity degree is increased, an accurate determination may be made whether or not the endoscope image P is obtained by the near view imaging.

Complexity degree detection means 50 may detect the complexity degree CD by detecting a pit pattern, as well as by performing the fractal analysis. More specifically, complexity degree detection means 50 detects a pit pattern by performing region integration processing on an edge portion EP using a known method. Then, it extracts the area, circumferential length, major axis length, circularity degree, and the like of the edge portion EP as characteristic amounts, and generates, as the complexity degree, a characteristic vector with the characteristic amounts as vector components. Then, from the characteristic vector, imaged state determination means 60 determines whether or not the complexity degree CD of the pit pattern is not less than set threshold value CDref by a known algorithm, such as vector support machine, neural network, or the like. In this case also, by making use of the fact that, in the near view imaging, densely congregated fine capillary images or irregularities on the surface of a subject will appear in the endoscope image P and the complexity degree is increased, an accurate determination may be made whether or not the endoscope image P is obtained by the near view imaging.

Condition changing means 70 is a means for automatically changing an imaging condition according to the imaged state determined by imaged state determination means 60. More specifically, when determined to be near view imaging, condition changing means 70 sets the magnification of imaging lens 21 of scope 20 greater (e.g., 60× or more) than a standard magnification (e.g., 20×). Further, condition changing means 70 controls light source unit 10 such that the amount of light emitted from light emitting means 16 is reduced. On the other hand, if the imaged state is determined to be distant view imaging, condition changing means 70 sets the magnification of imaging lens 21 of scope 20 smaller than the standard magnification (e.g., 1×). Further, condition changing means 70 controls light source unit 10 such that the amount of light emitted from light emitting means 16 is increased.

In this way, by automatically switching imaging modes according to the complexity degree CD of the endoscope image P, imaging conditions appropriate for a subject region the operator intends to observe are set automatically, thereby assisting in the operator to perform an endoscope observation efficiently by eliminating the need for the operator to set the imaging magnification as required in a conventional apparatus. That is, the near view imaging is, in general, imaging for a local region of a subject, and densely congregated fine capillaries, fine irregularities of a living tissue, a pit pattern, and the like will appear in the endoscope image, as shown in FIG. 2. Thus, the complexity degree CD of the endoscope image is increased. On the other hand, a contour of a large blood vessel, capillary, or living tissue appears in an endoscope image obtained by keeping the tip of scope 20 at a distance from the subject, as shown in FIG. 3, and the complexity degree CD becomes small compared with the near view enlargement imaging. Consequently, a region the operator intends to observe may be figured out based on the complexity degree CD, and the imaging mode may be automatically switched to that optimal for the estimated region. This will reduce the burden on the operator, thereby enabling the operator to efficiently perform an endoscope observation.

Figure 4:
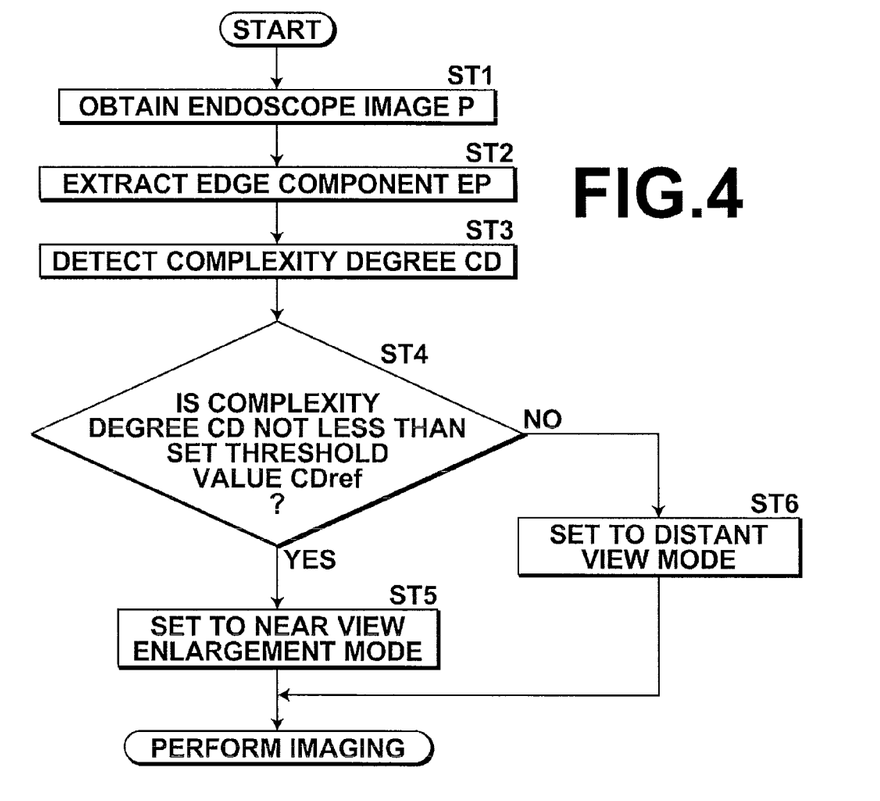
FIG. 4 is a flowchart illustrating a preferred embodiment of the control method of the endoscope apparatus of the present invention.

FIG. 4 is a flowchart illustrating a preferred embodiment of the control method of the endoscope apparatus of the present invention. The control method of the endoscope apparatus will now be described with reference to FIGS. 1 to 4. First, an endoscope image is obtained by performing imaging with scope 20 inserted into a body cavity (step ST1). Then, an edge portion EP is extracted from the endoscope image by edge extraction means 40 (step ST2). Thereafter, a complexity degree CD of the edge portion EP is detected (step ST3), and a determination is made by condition changing means 70 as to whether or not the complexity degree CD is not less than a set threshold value CDref (step ST4). If the complexity degree CD is not less than the set threshold value CDref, the imaging mode is set to the near view enlargement mode by condition changing means 70, and the magnification of imaging lens 21 is set to 30× to 60× by apparatus controller 80, and the amount of light emitted from light source 10 is reduced (step ST5). On the other hand, if the complexity degree CD is less than the set threshold value CDref, the imaging mode is set to the distant view imaging mode by condition changing means 70, the magnification of imaging lens 21 is set to 1× by apparatus controller 80, and the amount of light emitted from light source unit 10 is increased (step ST6).

According to the embodiment described above, an edge portion EP of an endoscope image P obtained by scope 20 is extracted, then a complexity degree CD of the extracted edge portion EP is detected, determination is made as to whether the endoscope image P is an image obtained by the near view imaging or distant view imaging a subject based on the detected complexity degree CD, the imaging conditions are switched according to the determined near view imaging or distant view imaging to figure out a region the operator intends to observe from endoscope image P, and the imaging mode is set to that appropriate for the intended observation region. This may eliminate the need for the operator to switch the imaging mode, thereby enabling the operator to perform image diagnosis efficiently.

In a case where imaged state determination means 60 is a means that determines an image to be obtained by the near view imaging when the complexity degree CD is not less than the set threshold value CDref and to be obtained by the distant view imaging when the complexity degree CD is less than the set threshold value CDref, an accurate determination may be made whether or not an endoscope image P is an image obtained by the near view imaging by making use of the fact that, in the near view imaging, densely congregated fine capillary images or irregularities on the surface of a subject will appear in the endoscope image P and the complexity degree is increased.

If complexity degree detection means 50 is a means that detects a fractal dimension of an edge portion EP as the complexity degree CD, the complexity degree CD may be detected accurately.

Further, if complexity degree detection means 50 is a means that extracts a pit pattern from an edge portion EP and detects a complexity degree CD of the extracted pit pattern, the complexity degree CD may be detected accurately.

Still further, if scope 20 has imaging lens 21 changeable in imaging magnification and condition changing means 70 is a means that increases the imaging magnification of imaging lens 21 for near view imaging and decreases the imaging magnification for distant view imaging, the imaging magnification is automatically set to a value appropriate for near view imaging, whereby image diagnosis may be performed efficiently.

Further, if scope 20 includes light emitting means 16 for emitting light to the subject, and condition changing means 70 decreases the amount of light emitted from light emitting means 16 for near view imaging and increases the amount of light emitted from light emitting means 16 when the imaging mode is switched to the distant view imaging, the amount of light is automatically set to a value appropriate for near view imaging, whereby image diagnosis may be performed efficiently.

The present invention is not limited to the embodiment described above. For example, in the embodiment described above, although the description has been made of a case in which a complexity degree CD is detected using an ordinary image obtained by emitting white light to a subject, the complexity degree CD may be detected using a narrowband image obtained by emitting narrowband light to the subject or a spectral image.

Further, in the embodiment described above, the description has been made of a case in which condition changing means 70 changes the imaging magnification and the amount of light as the imaging conditions, but image processing conditions of image processing means 33 may be changed, like emphasizing a high frequency component for near view imaging and emphasizing a low frequency component for distant view imaging, or increasing the magnification of electronic zoom for near view imaging and decreasing the magnification of electronic zoom for distant view imaging.

Still further, the description has been made of a case in which condition changing means 70 sets imaging conditions appropriate for distant view imaging when the complexity degree CD is less than the set threshold value CDref, but imaging lens 21 may be controlled such that the greater the complexity degree, the greater the magnification within the distant view imaging mode.

Figure 5:
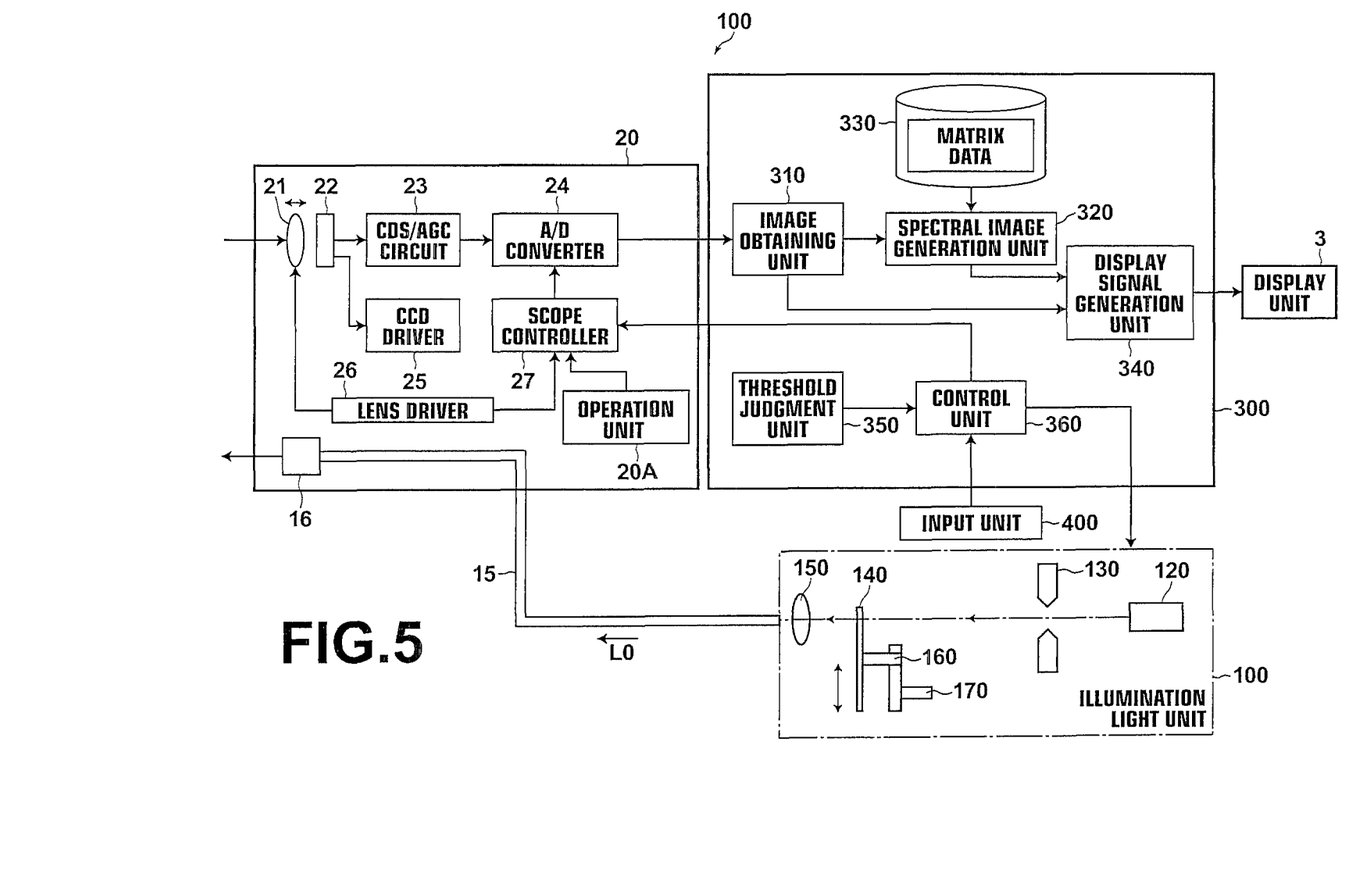
FIG. 5 is a block diagram of a second embodiment of the endoscope apparatus of the present invention.

Next, an endoscope apparatus incorporating a second embodiment of the present invention will be described in detail. FIG. 5 is a block diagram of endoscope apparatus 200 incorporating a second embodiment of the present invention, illustrating the schematic configuration thereof.

As shown in FIG. 5, endoscope apparatus 200 includes scope 20 to be inserted into a body cavity of a subject for observing an observation target, image processing unit 300 to which scope 20 is removably attached, illumination light unit 100, to which scope 20 is optically removably attached, for emitting illumination light L0, display unit 3 for displaying an observation target image based on a signal outputted from image processing unit 300, and input unit 400 for accepting input of specific information from the operator.

As shown in FIG. 5, illumination light unit 100 includes xenon lamp 120 for emitting white light, aperture 130 for controlling the amount of light emitted from xenon lamp 120, rotary filter 140 for turning the white light into frame sequential light, condenser lens 150 for condensing the frame sequential light provided by rotary filter 140 on the input face of light guide 15, rotary filter motor 160 for rotating rotary filter 140, and filter moving motor 170 for moving rotary filter in diameter directions (arrow directions in FIG. 5, i.e., directions perpendicular to the optical axis of rotary filter 140).

Figure 6:
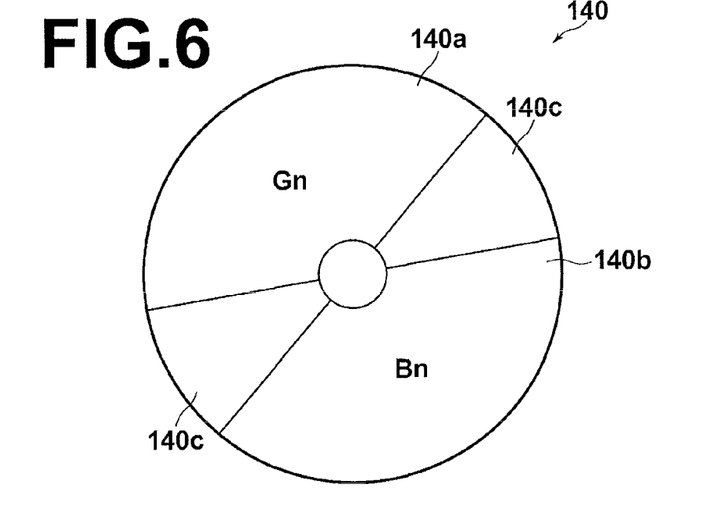
FIG. 6 illustrates a structure of a rotary filter of the endoscope apparatus shown in FIG. 5.

FIG. 6 illustrates a structure of rotary filter 140. As illustrated in FIG. 6, rotary filter 140 includes Gn filter 140a that transmits green narrow wavelength component (Gn component), Bn filter 140b that transmits blue narrow wavelength component (Bn component), and light blocking section 140c that blocks light.

Figure 7:
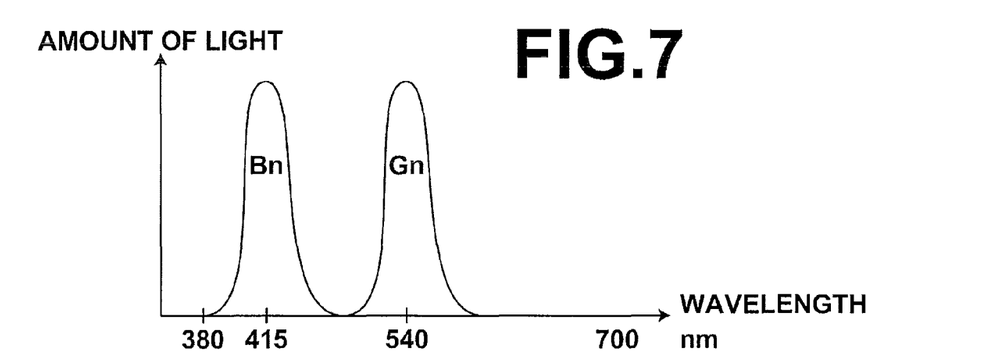
FIG. 7 illustrates an optical characteristic of the rotary filter of the endoscope apparatus shown in FIG. 5.

FIG. 7 illustrates a spectral characteristic of narrowband light beams outputted from each filter of rotary filter 140. Gn and Bn in FIG. 7 represent light beams transmitted through 140a and 140b respectively.

Each filter of rotary filter 140 is provided for imaging a narrowband image. A specific example of spectral characteristic for Gn filter 140a may be a bandpass characteristic with a center wavelength of 540 nm and a half bandwidth of 20 to 40 nm, and a specific example for Bn filter may be a bandpass characteristic with a center wavelength of 415 nm and a half bandwidth of 20 to 40 nm.

In the present embodiment, rotary filter 140 includes the filters having the aforementioned optical characteristics in order to obtain a narrowband image capable of representing a fine structure, such as a capillary or a pit pattern, but a narrowband filter having the other color or wavelength component may be used according to the application.

The configuration of scope 20 is substantially identical to that of scope 20 in the first embodiment.

The operation of image sensor 22 is controlled by CCD driver 25, in which a clock signal having a certain period is outputted to image sensor 22, and image sensor 22 sequentially outputs image signals according to the clock signal. The period of the clock signal is set to, for example, 1/60 s based on the frame rate of 60 fps for motion picture display. When an image signal is outputted from image sensor 22, the signal is sampled and amplified by CDS/AGC (correlated double sampling/automatic gain control) circuit 23, and the signal outputted from CDS/AGC circuit 23 is A/D converted by A/D converter 24 and the digital image signal is outputted to image processing unit 300.

The magnification of imaging lens 21 of scope 20 is changed based on a control signal from scope controller 27. More specifically, imaging lens 21 includes a concave lens and a convex lens, and the magnification is changed by moving the convex lens in the arrow directions in FIG. 5. In the present embodiment, the magnification of imaging lens 21 is changed through input by the operator from input unit 400.

Image processing unit 300 includes image signal obtaining unit 310 that obtains an image signal outputted from image sensor 22 of scope 20 when illumination light L0 is emitted onto an observation target, spectral image generation unit 320 that generates an estimated spectral image signal having a specific wavelength component by performing spectral image processing on the image signal obtained by image signal obtaining unit using estimated matrix data, storage unit 330 having stored therein the estimated matrix data used for performing the spectral image processing in spectral image generation unit 320, display signal generation unit 340 that generates a display image signal by performing various types of processing on the image signal outputted from image signal obtaining unit 310 or estimated spectral image signal outputted from spectral image generation unit 320, threshold judgment unit 350 that judges whether or not a magnification of imaging lens 21 inputted from input unit 400 is not less than a specific threshold value, and control unit 360 that controls image processing unit 300, scope 20, illumination light unit 100, and display unit 3. The operation of each unit will be described later.

Display unit 3, constituted by a liquid crystal display, CRT, or the like, is capable of displaying an ordinary image, a spectral image, or a narrowband image based on a display image signal outputted from image processing unit 300.

An operation of the endoscope apparatus of the present embodiment will be described.

Endoscope apparatus 200 of the present embodiment is configured so as to be switchable between an ordinary image display mode in which an ordinary image of an observation target is displayed and a specific wavelength image display mode in which a specific wavelength image of an observation target formed by extracting a specific frequency component is displayed. In the specific wavelength image display mode, the apparatus is further capable of switching between a narrowband image shooting mode and a spectral image shooting mode.

An operation of the apparatus in the ordinary mode will be described first.

First, the ordinary image display mode is selected by the operator through input unit 400. After an insertion section of scope 20 is inserted into a body cavity, xenon lamp 120 of illumination light unit 100 is activated based on a control signal from control unit 360 in image processing unit 300 and white light is emitted from xenon lamp 120.

Note that, at this time, rotary filter 140 is moved to a position away from the optical path of the white light emitted from xenon lamp 120, so that the white light emitted from xenon lamp 120 reaches one end of light guide 15 directly without passing through rotary filter 140.

The white light emitted from xenon lamp 120 is inputted to one end of light guide 15, and the white light guided through light guide 15 is outputted from the other end of light guide 15 and emitted to the observation target through observation window 16. Then, reflected light $L_R$ of the white light reflected from the observation target is inputted to imaging lens 21 of scope 20, and an image of the observation target is formed on the imaging plane of image sensor 22 by imaging lens 21. Initially, the magnification of imaging lens 21 is set to 1×, but it may be changed by the operator by inputting a desired magnification to input unit 400 after an ordinary image is displayed.

Then, an image of the observation target is picked up by image sensor 22 driven by CCD driver 25 and image signals constituted by R component, G component, and B component are sequentially outputted according to a clock signal from CCD driver 25.

Thereafter, the image signals are subjected to correlated double sampling and automatic gain control in CDS/AGC circuit 23, A/D converted in A/D converter 24, and inputted to image processing unit 300 as digital signals.

The image signals constituted by R component, G component, and B component outputted from scope 20 are obtained by image signal obtaining unit 310 of image processing unit 300. Then, image signal obtaining unit 310 sequentially outputs the obtained image signals to display signal generation unit 340.

Display signal generation unit 340 performs various types of signal processing on the inputted image signal and generates a Y/C signal constituted by a luminance signal Y and a color difference signal C. Then, display signal generation unit 340 generates a display image signal by further performing various types of signal processing, such as I/P conversion, noise reduction, and the like, on the Y/C signal and outputs the generated display image signal to display unit 3.

Display unit 3 displays an ordinary image of the observation target based on the inputted display image signal.

Figure 8:
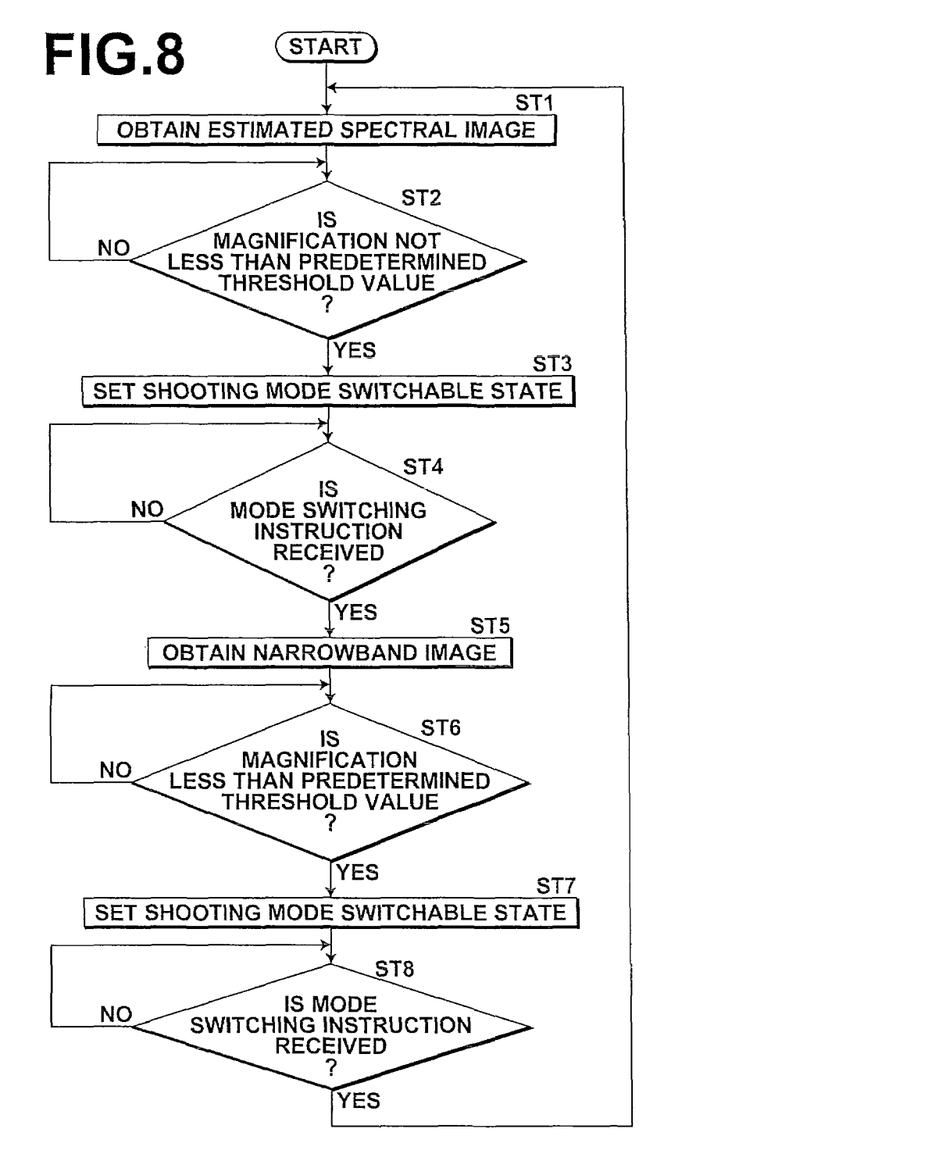
FIG. 8 is a flowchart illustrating an operation of the second embodiment of the endoscope apparatus of the present invention.

Next, an operation of the apparatus when the display mode is switched to the specific wavelength image display mode by the operator, while a motion picture of ordinary images is displayed in the ordinary image display mode described above, will be described with reference to the flowchart shown in FIG. 8.

First, the specific wavelength image display mode is selected by the operator through input unit 400.

The default setting of the specific wavelength image display mode is an estimated spectral image shooting mode and control unit 360 controls the apparatus so that an estimated spectral image is obtained.

More specifically, control unit 360 outputs a control signal to image signal obtaining unit 310 in response to a switching signal for switching to the specific wavelength image display mode outputted from input unit 400, and image signal obtaining unit 310 outputs an image signal to spectral image generation unit 320 according to the control signal.

Spectral image generation unit 320 performs spectral image processing on the image signal of R component, G component, and B component using estimated matrix data stored in storage unit 330.

More specifically, spectral image generation unit 320 performs a matrix operation represented by Formula (I) below and generates estimated spectral data ($q_1$ to $q_{59}$).

$$\begin{bmatrix} q_1 \\ q_2 \\ \vdots \\ q_{59} \end{bmatrix} = \begin{bmatrix} k_{1r} k_{1g} k_{1b} \\ k_{2r} k_{2g} k_{2b} \\ \vdots \\ k_{59r} k_{59g} k_{59b} \end{bmatrix} \times \begin{bmatrix} R \\ G \\ B \end{bmatrix} \quad (1)$$

The estimated matrix data include 59 wavelength range parameters obtained by dividing, for example, a wavelength range from 410 nm to 700 nm by an interval of 5 nm, and each wavelength range parameter includes coefficients $k_{pr}$, $k_{pg}$ and $k_{pb}$=1 to 59).

Then, for example, three wavelength ranges λ1, λ2, and λ3 are selected by the operation of input unit 400, and estimated spectral data corresponding to the three selected wavelength ranges are obtained. For example, when wavelengths 550 nm, 500 nm, and 470 nm are selected as the three wavelength ranges λ1, λ2, and λ3, estimated spectral data q29, q19, and q13 corresponding to the respective wavelength ranges are obtained.

Then, an appropriate gain offset is given to each of the calculated estimated spectral data q29, q19, and q13, which are respectively called pseudo three color image signals R', G', B' (estimated spectral image signals). In the present embodiment, such wavelengths as λ1, λ2, and λ3 described above are selected in order to make a color change in an observation target more recognizable, but other wavelengths may also be selected.

Then, the pseudo three color image signals R', G', B' are sequentially outputted to display signal generation unit 340, and display signal generation unit 340 performs various types of signal processing on the inputted pseudo three color image signal and generates a Y/C signal constituted by a luminance signal Y and a color difference signal C. Then, display signal generation unit 340 generates a display image signal by further performing various types of signal processing, such as I/P conversion, noise reduction, and the like, on the Y/C signal and outputs the generated display image signal to display unit 3.

Display unit 3 displays an estimated spectral image of the observation target having the specific wavelength components based on the inputted display image signal (step ST1).

When the specific wavelength image display mode is selected, an estimated spectral image is displayed first in the manner as described above. While the estimated spectral image is displayed, if the operator desires to observe a near view enlarged image, the tip of scope 20 is moved closer to the observation target and the magnification of imaging lens is increased through input unit 400.

The magnification of imaging lens 21 inputted by the operator through input unit 400 is inputted to control unit 360 of image processing unit 300, and the magnification is outputted to threshold judgment unit 350 and a control signal according to the inputted magnification is outputted from control unit 360 to scope 20.

The control signal according to the magnification of imaging lens 21 is inputted to scope controller 27 of scope 20, and scope controller 27 causes the concave lens of imaging lens 21 to be moved so that imaging lens 21 has the magnification inputted by the operator.

In the mean time, threshold judgment unit 350 judges whether or not the inputted magnification is not less than a specific threshold value determined in advance (step ST2). The threshold value may be any magnification within the range, for example, from 20× to 60×.

Then, if the inputted magnification of imaging lens 21 is judged, in threshold judgment unit 350, to be not less than the specific threshold value, the judgment result is outputted to control unit 360, and control unit 360 is set to a shooting mode switchable state (step ST3). When shooting mode switchable state is set, control unit 360 outputs a control signal to display unit 3 to cause display unit 3 to display a message or a mark notifying the operator that the apparatus is under the shooting mode switchable state.

After the apparatus is set to the shooting mode switchable state, the apparatus enters into a wait state for input by the operator of a switch instruction signal from the estimated spectral image shooting mode to the narrowband image shooting mode (step ST4). When the switch instruction signal is inputted by the operator through input unit 400, the instruction signal is outputted to control unit 360, and control unit 360 controls the apparatus so as to be changed to the narrowband image shooting mode (step ST5).

More specifically, control unit 360 outputs a control signal to illumination light unit 100 and, in response to the control signal, illumination light unit 100 moves the rotary filter 140 in the optical path of white light and starts rotating rotary filter 140.

The operation of rotary filter 140 causes Gn component light beam and Bn component light beam to be sequentially outputted from Gn filter 140a and Bn filter 140b of rotary filter 140, which are inputted to one end of light guide 15 through condenser lens 150.

The Gn component light beam and the Bn component light beam guided through light guide 15 are outputted from the other end of light guide 15 and emitted to the observation target through observation window 16. Then reflected light beams $L_G$ and $L_B$ of these light beams reflected from the observation target are sequentially inputted to imaging lens 21 of scope 20, and an image of the observation target is formed on the imaging plane of image sensor 22 by imaging lens 21. Then image sensor 22 driven by CCD driver 25 picks up the image of the observation target and sequentially outputs image signals of Gn component and Bn component. Then, the image signals are subjected to correlated double sampling and automatic gain control in CDS/AGC circuit 23, A/D converted in A/D converter 24, and inputted to image processing unit 300 as digital signals.

The image signals of Gn component and Bn component are obtained by image signal obtaining unit 310 of image processing unit 300. Then, image signal obtaining unit 310 outputs the image signals of Gn component and Bn component to display signal generation unit 340.

Display signal generation unit 340 performs various types of signal processing on the inputted image signals of Gn component and Bn component and generates a Y/C signal constituted by a luminance signal Y and a color difference signal C. Then, display signal generation unit 340 generates a display image signal by further performing various types of signal processing, such as I/P conversion, noise reduction, and the like, on the Y/C signal and outputs the generated display image signal to display unit 3. Display unit 3 displays a narrowband image of the observation target based on the inputted display image signal.

In the present embodiment, image signals of Gn component and Bn component are obtained as the narrowband image signal and, based on these image signals, a display image signal representing a narrowband image is generated. But, for example, only the image signal of Gn component may be obtained and the display image signal representing the narrowband image may be generated based only on the image signal of Gn component, or only the image signal of Bn component may be obtained and the display image signal representing the narrowband image may be generated based only on the image signal of Bn component.

After the apparatus is switched to the narrowband image shooting mode and while a narrowband image of the observation target is displayed, if the operator desires to observe a distant view image of the observation target, the tip of scope 20 is moved away from the observation target and the magnification of imaging lens is decreased through input unit 400.

The magnification of imaging lens 21 inputted by the operator through input unit 400 is inputted to control unit 360 of image processing unit 300, and the magnification is outputted to threshold judgment unit 350 and a control signal according to the inputted magnification is outputted from control unit 360 to scope 20.

The control signal according to the magnification of imaging lens 21 is inputted to scope controller 27 of scope 20, and scope controller 27 causes the concave lens of imaging lens 21 to be moved so that imaging lens 21 has the magnification inputted by the operator.

In the mean time, threshold judgment unit 350 judges whether or not the inputted magnification is less than a specific threshold value determined in advance (step ST6).

Then, if the inputted magnification of imaging lens 21 is judged, in threshold judgment unit 350, to be less than the specific threshold value, the judgment result is outputted to control unit 360, and control unit 360 is set to a shooting mode switchable state (step ST7). When shooting mode switchable state is set, control unit 360 outputs a control signal to display unit 3 to cause display unit 3 to display a message or a mark notifying the operator that the apparatus is under the shooting mode switchable state.

After the apparatus is set to the shooting mode switchable state, the apparatus enters into a wait state for input by the operator of a switch instruction signal from the narrowband image shooting mode to the estimated spectral image shooting mode (step ST8). When the switch instruction signal is inputted by the operator through input unit 400, the instruction signal is outputted to control unit 360, and control unit 360 controls the apparatus so as to be switched to the estimated spectral image shooting mode again (step ST1).

As described above, in the specific wavelength image display mode of the present embodiment, the apparatus is set to shooting mode switchable state according to the magnification of imaging lens 21, and the shooting mode is switched when a shooting mode switch instruction is received from the operator.

So far the operation of the specific wavelength image display mode of the endoscope apparatus of the present embodiment has been described.

Figure 9:
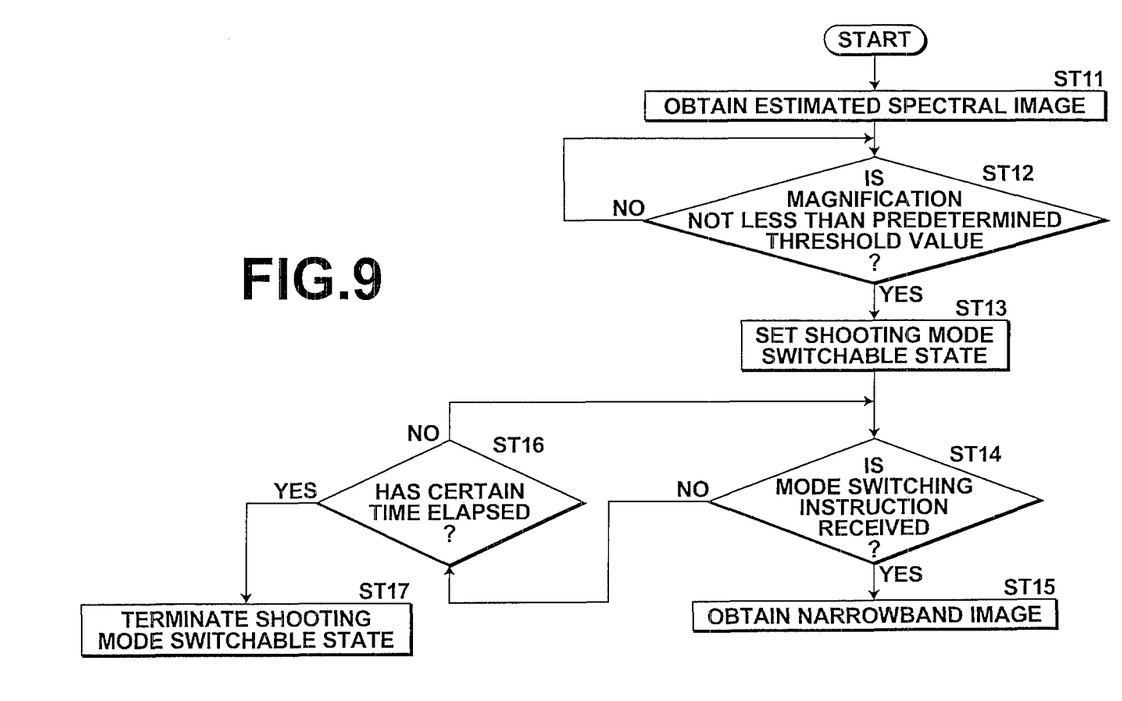
FIG. 9 is a flowchart illustrating an operation of a first modification of the second embodiment of the endoscope apparatus of the present invention.

In the specific wavelength image display mode of the present embodiment, after the apparatus is set to shooting mode switchable state (steps ST3, ST7), if a mode switch instruction is received from the operator (steps ST4, ST8), shooting mode is changed. But an arrangement may be adopted, for example as in the flowchart shown in FIG. 9, in which after shooting mode switchable state has been set (step ST13), if a mode switch instruction is not received from the operator for a certain time (steps ST14, ST16), the shooting mode switchable state in control unit 360 is terminated (step ST17). Note that the steps ST11 to ST13 of the flowchart shown in FIG. 9 are identical to the steps ST1 to ST3 shown in FIG. 8. The flowchart shown in FIG. 9 illustrates a case in which the mode is switched from the estimated spectral image shooting mode to the narrowband image shooting mode, but identical steps are performed when the mode is switched from the narrowband image shooting mode to the estimated spectral image shooting mode.

Figure 10:
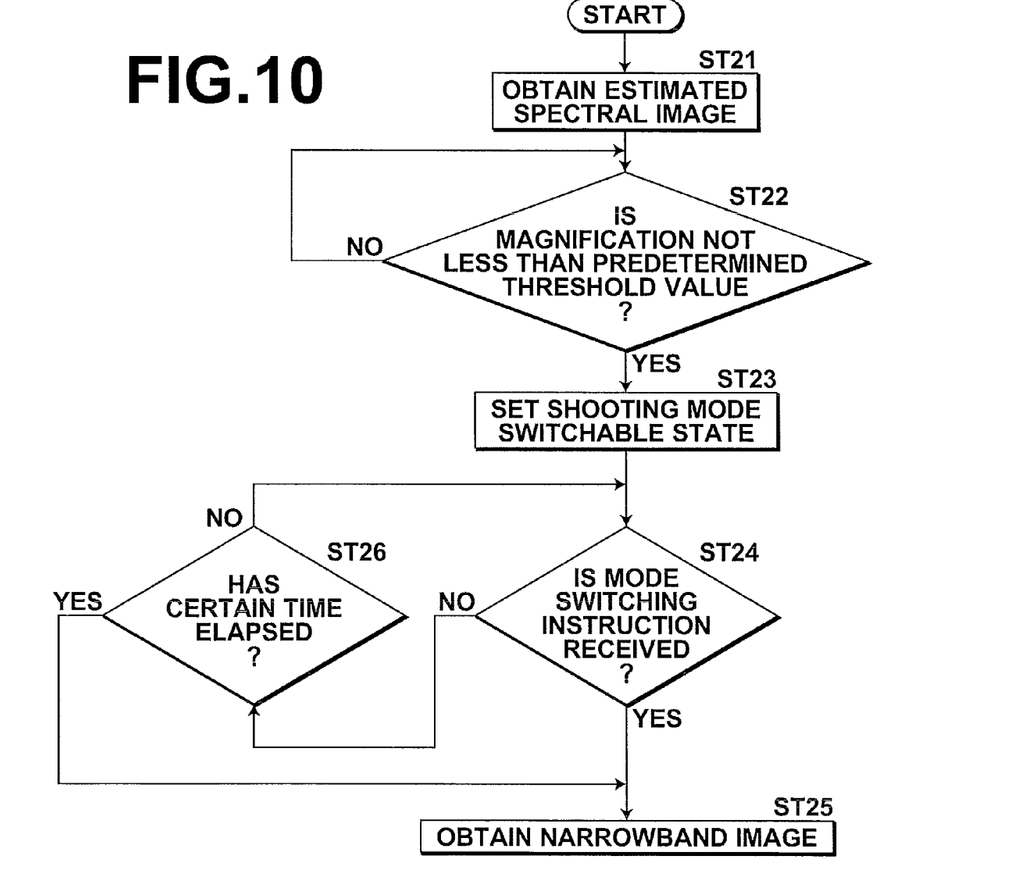
FIG. 10 is a flowchart illustrating an operation of a second modification of the second embodiment of the endoscope apparatus of the present invention.

Further an arrangement may be adopted, for example as in the flowchart shown in FIG. 10, in which after shooting mode switchable state has been set (step ST23), if a mode switch instruction is not received from the operator for a certain time (steps ST24, ST26), the shooting mode is forcibly switched by control unit 360 regardless of whether or not a mode switch instruction is issued (step ST25). Note that the steps ST21 to ST23 of the flowchart shown in FIG. 10 are identical to the steps ST1 to ST3 shown in FIG. 8. The flowchart shown in FIG. 10 illustrates a case in which the mode is switched from the estimated spectral image shooting mode to the narrowband image shooting mode, but identical steps are performed when the mode is switched from the narrowband image shooting mode to the estimated spectral image shooting mode.

In the endoscope apparatus of the present embodiment, a judgment is made as to whether or not shooting mode switchable state is set through a threshold judgment of the magnification of the zoom lens by threshold judgment unit 350. But, for example, when the magnification of an observation target image is changed by digital zoom instead of a zoom lens, a configuration may be adopted in which the magnification of the digital zoom is threshold-judged by threshold judgment unit 350.

Further, the target of threshold judgment in threshold judgment unit 350 is not limited to the magnification and, for example, luminance signal Y generated in display signal generation unit 340 may be the target of threshold judgment. More specifically, an arrangement may be adopted in which luminance signal Y generated in display signal generation unit 340 is inputted to threshold judgment unit 350 and, for example, in estimated spectral image shooting mode, if the inputted luminance signal Y is judged to be not less than a specific threshold value, control unit 360 is set to shooting mode switchable state, or in narrowband image shooting mode, if the inputted luminance signal Y is judged to be less than a specific threshold value, control unit 360 is set to shooting mode switchable state. The threshold value may be, for example, any value within the range from 20 to 40% of a maximum value of luminance signal Y.

Still further, the target of threshold judgment in threshold judgment unit 350 is not limited to the magnification or luminance signal described above, and any parameter may be used as long as it varies according to the distance between the tip of scope 20 and observation target.

Further, in the endoscope apparatus of the present embodiment, the magnification of imaging lens 21 is changed by the operator, but the magnification may be changed automatically based on the magnitude of luminance signal Y generated in display signal generation unit 340. More specifically, the magnification of imaging lens 21 is set such that the greater the luminance signal Y, the greater the magnification. Then, the automatically changed magnification may be threshold-judged in threshold judgment unit 350.

Still further, in the endoscope apparatus of the present embodiment, shooting mode is switched when a shooting mode switch instruction is received from the operator after entering into shooting mode switchable state. But, an arrangement may be adopted in which the shooting mode is switched when a shooting mode switch instruction is received from the operator before entering into shooting mode switchable state or the shooting mode is made unswitchable if a shooting mode switch instruction is received from the operator before entering into shooting mode switchable state.

What is claimed is:

1. An endoscope apparatus, comprising:
a scope for obtaining an endoscope image by imaging a subject;
an edge extractor configured to extract an edge component of the endoscope image obtained by the scope;
a complexity degree detector configured to detect a complexity degree of the edge component extracted by the edge extractor;
an imaged state determination unit configured to determine whether the endoscope image is an image obtained through near view imaging or distant view imaging of the subject according to the complexity degree detected by the complexity degree detector; and
a condition changing unit configured to change an imaging condition according to the near view imaging or distant view imaging determined by the imaged state determination unit, wherein
the imaged state determination unit determines the endoscope image to be an image obtained by the near view imaging if the complexity degree is not less than a set threshold value and to be an image obtained by the distant view imaging if the complexity degree is less than the set threshold value.

2. The endoscope apparatus of claim 1, wherein the complexity degree is a fractal dimension of the edge component.

3. The endoscope apparatus of claim 1, wherein the complexity degree detector detects the complexity degree of the edge component by extracting a pit pattern from the edge component and detecting a complexity degree of the extracted pit pattern.

4. The endoscope apparatus of claim 1, wherein:
the scope has an imaging lens changeable in imaging magnification; and
the condition changing unit increases the magnification of the imaging lens for the near view imaging and decreases the magnification of the imaging lens for the distant view imaging.

5. The endoscope apparatus of claim 1, wherein:
the scope includes a light emitter configured to emit light to the subject; and
the condition changing unit decreases the amount of the light emitted from the light emitter for the near view imaging and increases the amount of the light emitted from the light emitter for the distant view imaging.

6. A method for controlling an endoscope apparatus that obtains an endoscope image by imaging a subject with a scope, the method comprising:
extracting an edge component of the endoscope image obtained by the scope;
detecting a complexity degree of the extracted edge component;
determining whether the endoscope image is an image obtained through near view imaging or distant view imaging of the subject according to the detected complexity degree; and
changing an imaging condition according to the determined near view imaging or distant view imaging, wherein
said determining determines the endoscope image to be an image obtained by the near view imaging if the complexity degree is not less than a set threshold value and to be an image obtained by the distant view imaging if the complexity degree is less than the set threshold value.

7. An image obtaining method for use in an endoscope apparatus that includes a scope having an image sensor for picking up an image of an observation target, the method comprising:
enabling illumination light and narrowband light to be switchably emitted to the observation target;
enabling switching between an estimated spectral image signal obtaining mode, in which the illumination light is emitted to the observation target and an estimated spectral image signal is obtained by performing spectral image processing, using a predetermined signal processing parameter, on an image signal outputted from the image sensor by the emission of the illumination light, and a narrowband image signal obtaining mode, in which the narrowband light is emitted to the observation target and a narrowband image signal outputted from the image sensor by the emission of the narrowband light is obtained;
obtaining a parameter according to a distance between a tip portion of the scope and the observation target;

performing a threshold judgment on the obtained parameter and accepting a switching signal for switching between the estimated spectral image signal obtaining mode and the narrowband image signal obtaining mode; and obtaining the estimated spectral image signal or the narrowband image signal by switching between the estimated spectral image signal obtaining mode and the narrowband image signal obtaining mode based on a result of the threshold judgment and the switching signal.

8. An endoscope apparatus, comprising:

a light source unit capable of switchably outputting illumination light and narrowband light to be emitted to an observation target;

a scope having an image sensor for picking up an image of the observation target by receiving reflected light reflected from the observation target by the emission of the illumination light or the narrowband light to the observation target;

a parameter obtaining unit for obtaining a parameter according to a distance between a tip portion of the scope and the observation target;

a threshold judgment unit for performing a threshold judgment on the parameter obtained by the parameter obtaining unit;

a spectral image obtaining unit for obtaining an estimated spectral image signal by performing spectral image processing, using a predetermined signal processing parameter, on an image signal outputted from the image sensor by the emission of the illumination light to the observation target;

a narrowband image obtaining unit for obtaining a narrowband image signal outputted from the image sensor by the emission of the narrowband light to the observation target;

a switching signal accepting unit for accepting a switching signal for switching between obtaining of the estimated spectral image signal and obtaining of the narrowband image signal; and a control unit for switching between emission of the illumination light and emission of the narrowband light in the light source unit based on a judgment result of the threshold judgment unit and the switching signal, and controlling the light source unit, spectral image obtaining unit, and narrowband image obtaining unit to cause switching between obtaining of the estimated spectral image signal and obtaining of the narrowband image signal.

9. The endoscope apparatus of claim 8, wherein the control unit is a unit that sets a switchable state when the judgment result of the threshold judgment unit is changed and, if a switching signal is accepted by the switching signal accepting unit after the switchable state has been set, performs switching between emission of the illumination light and emission of the narrowband light and switching between obtaining of the estimated spectral image signal and obtaining of the narrowband image signal.

10. The endoscope apparatus of claim 9, wherein the control unit is a unit that, if a switching signal is not received by the switching signal accepting unit for a certain time after the switchable state has been set, terminates the switchable state.

11. The endoscope apparatus of claim 9, wherein the control unit is a unit that, if a switching signal is not received by the switching signal accepting unit for a certain time after the switchable state has been set, performs switching between emission of the illumination light and emission of the narrowband light and switching between obtaining of the estimated spectral image signal and obtaining of the narrowband image signal regardless of whether or not a switching signal is received.

12. The endoscope apparatus of claim 8, further comprising a notification unit for notifying that the apparatus is set to the switchable state.

13. The endoscope apparatus of claim 8, wherein the scope is a scope having an imaging lens for forming an image of the observation target on the image sensor by optically changing the magnification of the image, and the parameter is a value representing the magnification of the imaging lens.

14. The endoscope apparatus of claim 8, wherein the apparatus further comprises a digital zoom processing unit that performs digital zoom processing on an image signal outputted from the image sensor, and the parameter is a value representing a magnification of the digital zoom processing.

15. The endoscope apparatus of claim 8, wherein the parameter is luminance information of an image signal outputted from the image sensor.

* * * * *

UNITED STATES PATENT AND TRADEMARK OFFICE
CERTIFICATE OF CORRECTION

| | | |
|---|---|---|
| PATENT NO. | : 8,553,075 B2 | Page 1 of 1 |
| APPLICATION NO. | : 12/603187 | |
| DATED | : October 8, 2013 | |
| INVENTOR(S) | : Masahiro Kubo et al. | |

It is certified that error appears in the above-identified patent and that said Letters Patent is hereby corrected as shown below:

ON THE TITLE PAGE:

At item (30), Foreign Application Priority Data, change the second identified Japanese priority application from:

"Dec. 22, 2008 (JP) .................. 2005-325256" to

--Dec. 22, 2008 (JP) .................. 2008-325256--.

Signed and Sealed this
Eleventh Day of February, 2014

Michelle K. Lee
*Deputy Director of the United States Patent and Trademark Office*